US012611481B2

(12) United States Patent
Sakamoto

(10) Patent No.: US 12,611,481 B2
(45) Date of Patent: Apr. 28, 2026

(54) AIR CLEANING DEVICE

(71) Applicant: ALPS ALPINE CO., LTD., Tokyo (JP)

(72) Inventor: Hideki Sakamoto, Iwaki (JP)

(73) Assignee: ALPS ALPINE CO., LTD., Tokyo (JP)

( * ) Notice: Subject to any disclaimer, the term of this patent is extended or adjusted under 35 U.S.C. 154(b) by 1001 days.

(21) Appl. No.: 17/830,554

(22) Filed: Jun. 2, 2022

(65) Prior Publication Data

US 2023/0024952 A1      Jan. 26, 2023

(30) Foreign Application Priority Data

Jul. 20, 2021    (JP) ................................. 2021-119598

(51) Int. Cl.
   *A61L 9/20*        (2006.01)
(52) U.S. Cl.
   CPC ........... *A61L 9/205* (2013.01); *A61L 2209/12* (2013.01)
(58) Field of Classification Search
   CPC .. A61L 9/205; A61L 2209/12; A61L 2209/14; A61L 9/20; A61L 2209/134; A61L 2209/111; A61L 2209/22; A61L 2209/11; B60H 3/0658; B60H 3/0641; B60H 2003/0675; B60H 2003/0691; B01D 53/885; B01D 46/0036; B01D 2255/802; B01D 2259/4566; B01D 2259/804; B01D 2257/708; B01D 2255/20707; B01D 2258/06; B01D 2259/802; B01D 2253/102; B01D 2257/90; F04D 29/005; F04D 25/088
   See application file for complete search history.

(56) References Cited

U.S. PATENT DOCUMENTS

| | | | |
|---|---|---|---|
| 5,919,422 | A | 7/1999 | Yamanaka et al. |
| 2017/0197493 | A1 | 7/2017 | Paranhos et al. |
| 2019/0263226 | A1* | 8/2019 | Gruenbeck ............. A61L 9/205 |

FOREIGN PATENT DOCUMENTS

| | | | |
|---|---|---|---|
| JP | 3207938 U | 12/2016 | |
| KR | 2018-0129215 A | 12/2018 | |
| WO | WO 2022/051464 A1 | 3/2022 | |
| WO | WO-2022200239 A1* | 9/2022 | ........... F04D 29/005 |

OTHER PUBLICATIONS

Extended European Search Report for European Patent Application No. 22181272.0 dated Dec. 16, 2022, 9 pages.

* cited by examiner

*Primary Examiner* — Xiuyu Tai
(74) *Attorney, Agent, or Firm* — Crowell & Moring LLP

(57)        ABSTRACT

In an air-outlet unit that forms an air outlet of an air conditioner in an automobile, a light-emission control unit controls, in accordance with the airflow rate of the air conditioner that is obtained from an air-conditioning control device of the automobile, an LED driving unit that drives an LED array in such a manner that the amount of light that is emitted from the LED array and that activates a photocatalytic filter increases as the airflow rate of the air conditioner increases. The light that is emitted from the LED array is visible light, and some of the light that is reflected by the photocatalytic filter transmits to an area outside of the air-outlet unit by passing through fins that adjust the direction and the flow rate of the air blown by the air-outlet unit.

5 Claims, 11 Drawing Sheets

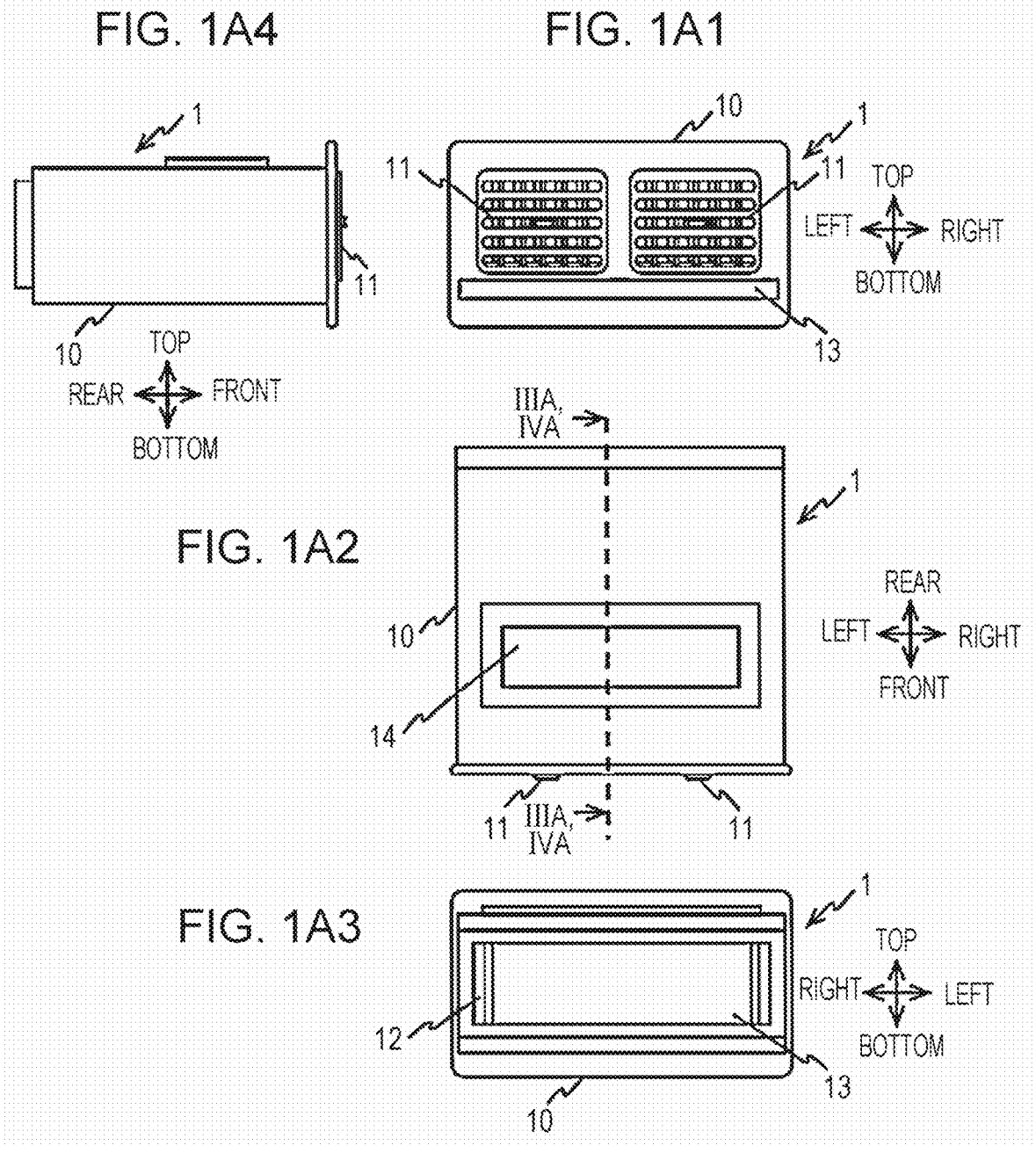
FIG. 1A4
FIG. 1A1
FIG. 1A2
FIG. 1A3

FIG. 1B1
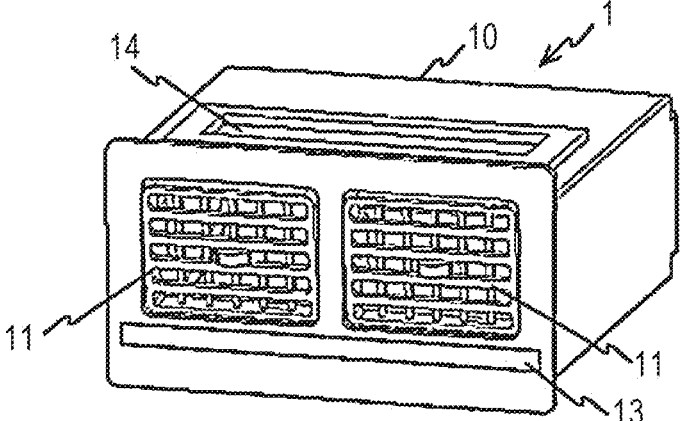
FIG. 1B2
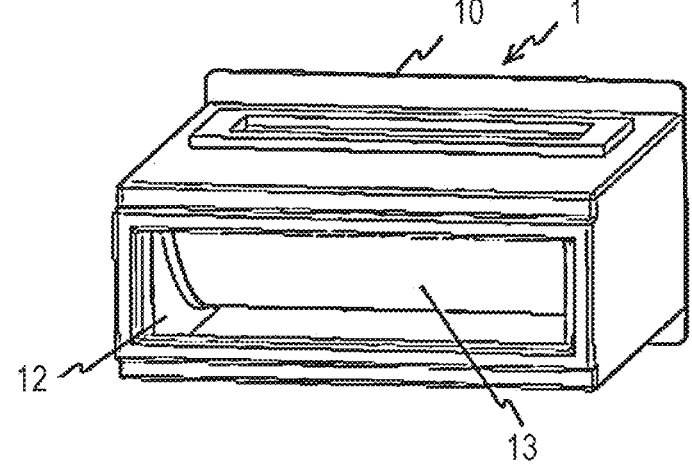

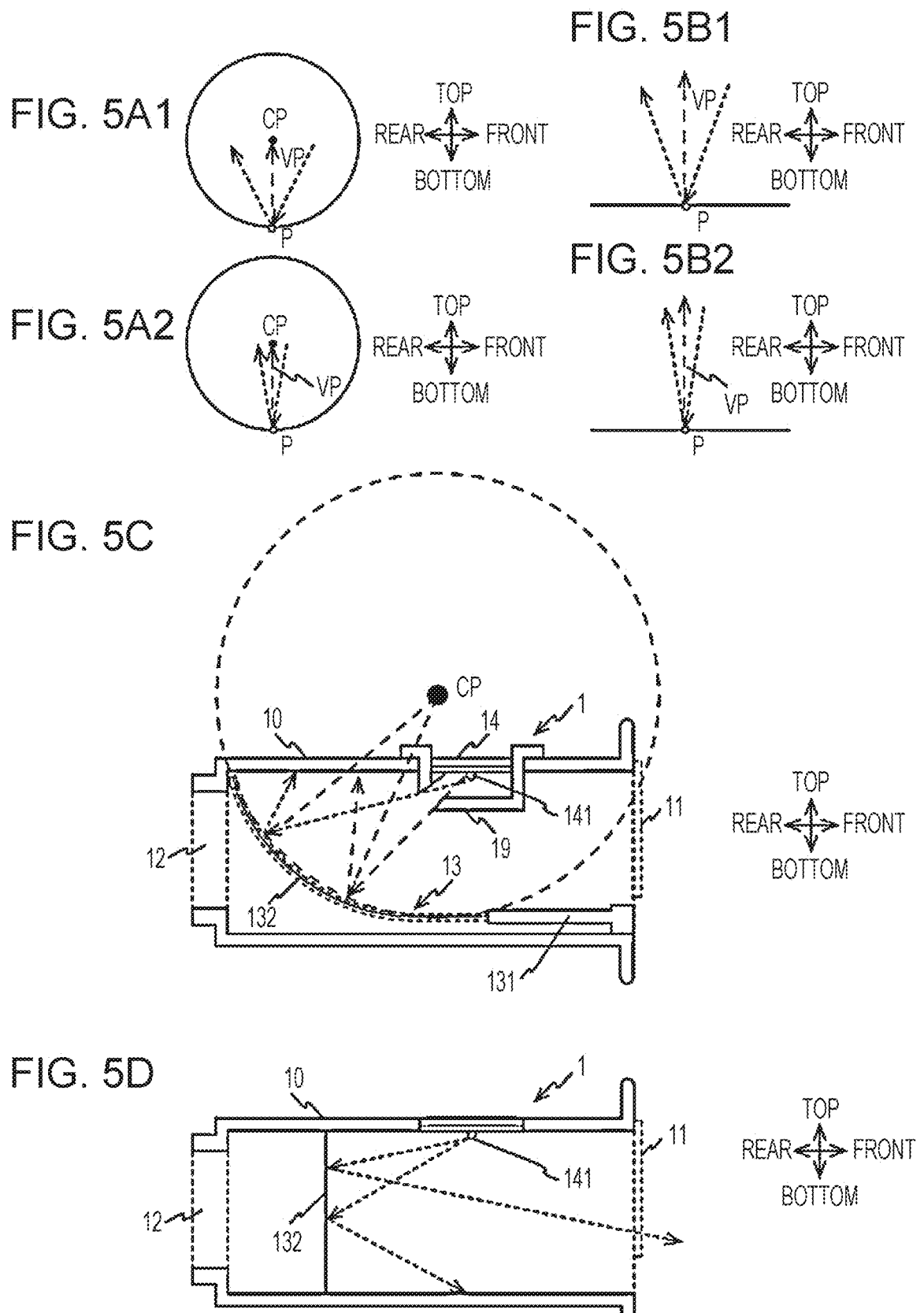

AIR CLEANING DEVICE

RELATED APPLICATION

The present application claims priority to Japanese Patent Application Number 2021-119598, filed on Jul. 20, 2021, the entirety of which is hereby incorporated by reference.

BACKGROUND

Field

The present disclosure relates to a technology for cleaning air to be supplied.

Description of the Related Art

There is known a technology for attaching an air cleaning device that is equipped with a photocatalytic filter and a light emitting diode (LED), which activates the photocatalytic filter, so as to cover an air outlet of an automobile with the air cleaning device. such that air that is sent to the air cleaning device through the air outlet of the automobile passes through the photocatalytic filter and is supplied to the vehicle cabin (see e.g., Japanese Registered Utility Model No. 3207938).

As an LED for activating a photocatalytic filter, it is necessary to use a short-wavelength, high-voltage LED, and thus, the above-mentioned air cleaning device has problems in that energy consumption (power consumption) is increased, and in that the service life of the LED is reduced if the LED is caused to continuously to emit light with a strong power in order to obtain a sufficiently high cleaning effect.

In addition, there has been a problem in that a user cannot directly perceive an air conditioning operation, so that it is difficult for the user to feel a benefit of the air cleaning device. Although providing a device, such as an indicator, that indicates an air cleaning operation enables a user to perceive the air cleaning operation, the manufacturing costs are increased by the additional costs for this device.

SUMMARY

Accordingly, it is an object of the present disclosure to achieve energy savings and extend the service life of an LED for activating a photocatalytic filter, while suppressing a reduction in an air cleaning effect.

In addition, it is another object of the present disclosure to enable a user to directly perceive an air cleaning operation, while suppressing an increase in the manufacturing costs.

The present disclosure provides an air cleaning device having an air supply port through which air is blown to outside from an inner space of the air cleaning device, the air cleaning device including a light emitting diode (LED) that emits light to the inner space, a photocatalytic filter that is disposed in the inner space and that cleans air blown by the air cleaning device by being activated by light emitted from the LED, an airflow rate sensor that detects a flow rate of the air blown by the air cleaning device, and a light-amount control unit that controls an amount of light that is emitted from the LED. Here, the light-amount control unit controls the amount of light that is emitted from the LED in such a manner that the amount of light increases as the airflow rate detected by the airflow rate sensor increases.

In such an air cleaning device, the LED may emit visible light, and some of the light emitted from the LED may transmit to outside from the air supply port.

In addition, the air cleaning device may be configured such that the light emitted from the LED does not directly transmit to the outside from the air supply port, and is directly incident on the photocatalytic filter, such that light that is reflected by the photocatalytic filter does not directly transmit to the outside from the air supply port, and such that at least some of light that is reflected by the photocatalytic filter after being directly incident on the photocatalytic filter from the LED and that is further reflected once or more transmits to the outside from the air supply port.

In addition, the LED may emit visible blue light. Furthermore, the air cleaning device may form an air outlet of an air conditioner of an automobile.

According to such an air cleaning device, the amount of light that is emitted from the LED increases as the airflow rate increases, so that in the case where a sufficient air cleaning effect is obtained with a low airflow rate and a relatively low air cleaning performance, energy saving of the LED and extension of the service life of the LED can be achieved by reducing the amount of light of the LED. In the case where the air flow rate is high and where a relatively high air cleaning performance is necessary in order to obtain a sufficient air cleaning effect, the sufficient air cleaning effect can be ensured by increasing the amount of light of the LED.

In addition, in the case where the LED emits visible light and where some of the light emitted from the LED transmits to the outside from the air supply port, a user can directly perceive an air cleaning operation of the air cleaning device by the transmitting light.

Furthermore, as the air cleaning that is performed increases, the intensity of the light that transmits to the outside is increased, and thus, the user can also directly and dynamically perceive the degree of the air cleaning by the intensity of this light. Therefore, without adding any special device to the air cleaning device, a user can directly recognize the air cleaning operation of the air cleaning device.

As described above, according to the present disclosure, energy saving and extension of the service life of an LED for activating a photocatalytic filter can be achieved, while a reduction in an air cleaning effect is suppressed.

In addition, a user can directly perceive an air cleaning operation, while an increase in the manufacturing costs is suppressed.

BRIEF DESCRIPTION OF THE DRAWINGS

FIGS. 1A1 to 1B2 are diagrams illustrating the appearance of an air-outlet unit according to an embodiment of the present disclosure;

FIGS. 2A1 to 2B are diagrams illustrating a filter module according to the embodiment of the present disclosure;

FIGS. 5A1 to 5D are diagrams illustrating how to determine the arrangement of the LED array and the photocatalytic filter according to the embodiment of the present disclosure;

DESCRIPTION OF THE PREFERRED EMBODIMENTS

Figure 2B:
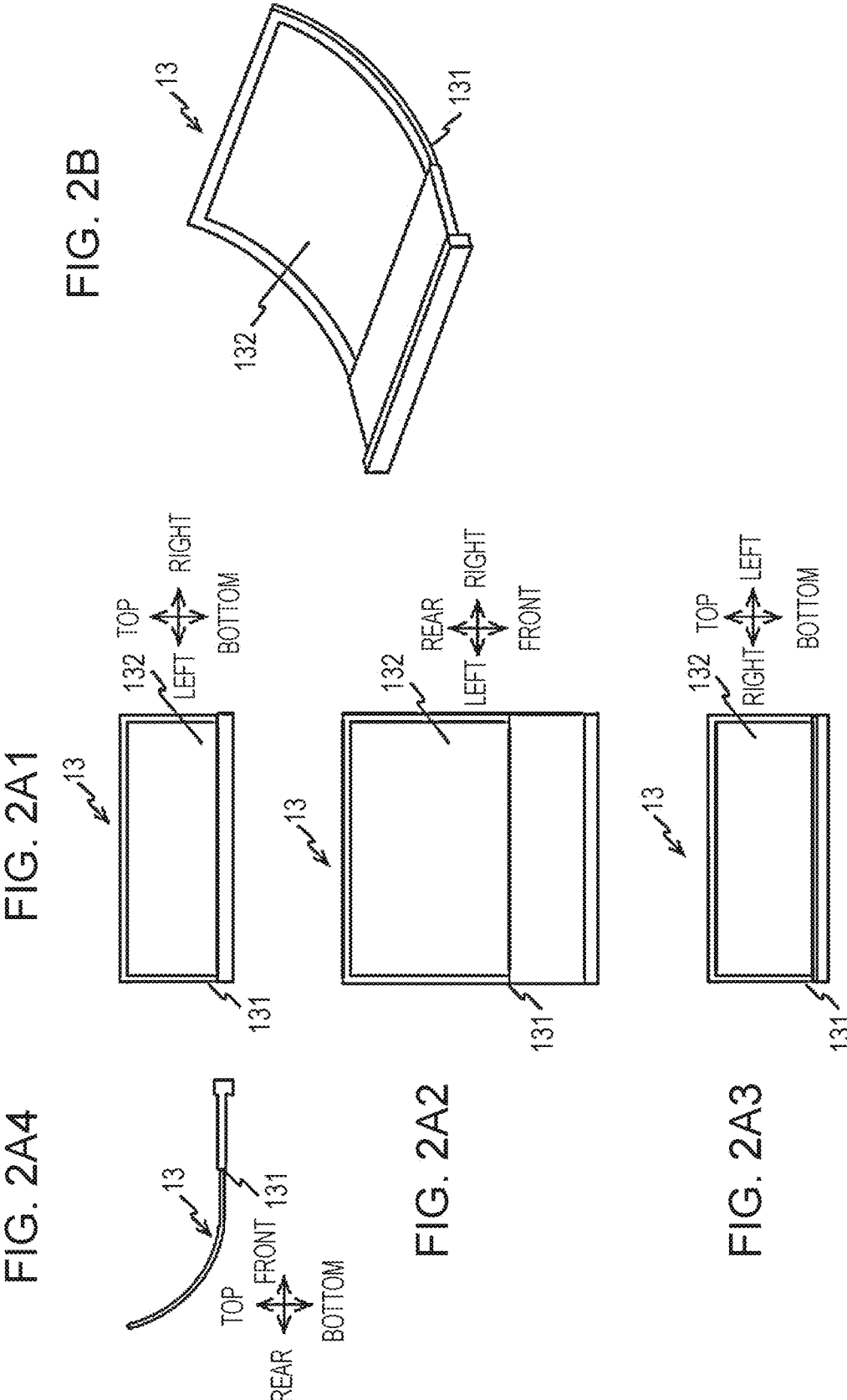

An embodiment of an air-outlet unit according to the present disclosure will be described below.

The air-outlet unit is a unit that is attached to an automobile so as to introduce air sent from an air duct 60 of an air conditioner of the automobile into the interior of the automobile and that forms an air outlet of the air conditioner of the automobile.

FIGS. 1A1 to 1B2 are diagrams illustrate the appearance of an air-outlet unit 1 according to the present embodiment. The front, rear, left, right, top, and bottom of the air-outlet unit 1 are defined as illustrated in FIGS. 1A1 to 1B2. FIG. 1A1 illustrates the front surface of the air-outlet unit 1. FIG. 1A2 illustrates the top surface of the air-outlet unit 1. FIG. 1A3 illustrates the rear surface of the air-outlet unit 1. FIG. 1A4 illustrates the left side surface of the air-outlet unit 1. Note that the right side surface of the air-outlet unit 1 is similar to the left side surface of the air-outlet unit 1.

FIG. 1B1 is a front perspective view of the air-outlet unit 1, as viewed from above, and FIG. 1B2 is a rear perspective view of the air-outlet unit 1, as viewed from above.

As illustrated in FIGS. 1A1 to 1B2, the air-outlet unit 1 includes a main body 10 that has a substantially rectangular shape with a hollow space formed therein.

The front surface of the main body 10 is provided with two fins 11 that adjust the direction and the flow rate of air and that form a path of the air between the hollow space and a space in front of the main body 10. The rear surface of the main body 10 has an inflow port 12, which is an opening, and the inflow port 12 is coupled to the air duct 60 of the air conditioner of the automobile.

A filter module 13 is disposed in the hollow space of the main body 10 so as to be replaceable, and a front end portion of the filter module 13 is exposed at the front surface of the main body 10. In addition, a light-source substrate 14 is disposed on an upper portion of the main body 10.

The configuration of the filter module 13 will now be described with reference to FIGS. 2A1 to 2B.

FIG. 2A1 illustrates the front surface of the filter module 13. FIG. 2A2 illustrates the top surface of the filter module 13. FIG. 2a3 illustrates the rear surface of the filter module 13. FIG. 2A4 illustrates the left side surface of the filter module 13. Note that the right side surface of the filter module 13 is similar to the left side surface of the filter module 13.

FIG. 2B is a front perspective view of the filter module 13, as viewed from above.

As illustrated in FIGS. 2A1 to 2B, the filter module 13 is a plate-shaped member whose rear portion is curved upward and includes a frame 131 and a photocatalytic filter 132.

The frame 131 has an opening formed in a rear portion of the frame 131 that is thinner than a front portion of the frame 131, and this rear portion is curved upward. In addition, a front end portion of the front portion of the frame 131 is formed to be slightly thicker.

The photocatalytic filter 132 is supported by the frame 131 in such a manner as to cover the opening formed in the rear portion of the frame 131. The photocatalytic filter 132 is a thin sheet-shaped member and is breathable.

Figures 3A, 3B, 3C, 3D:
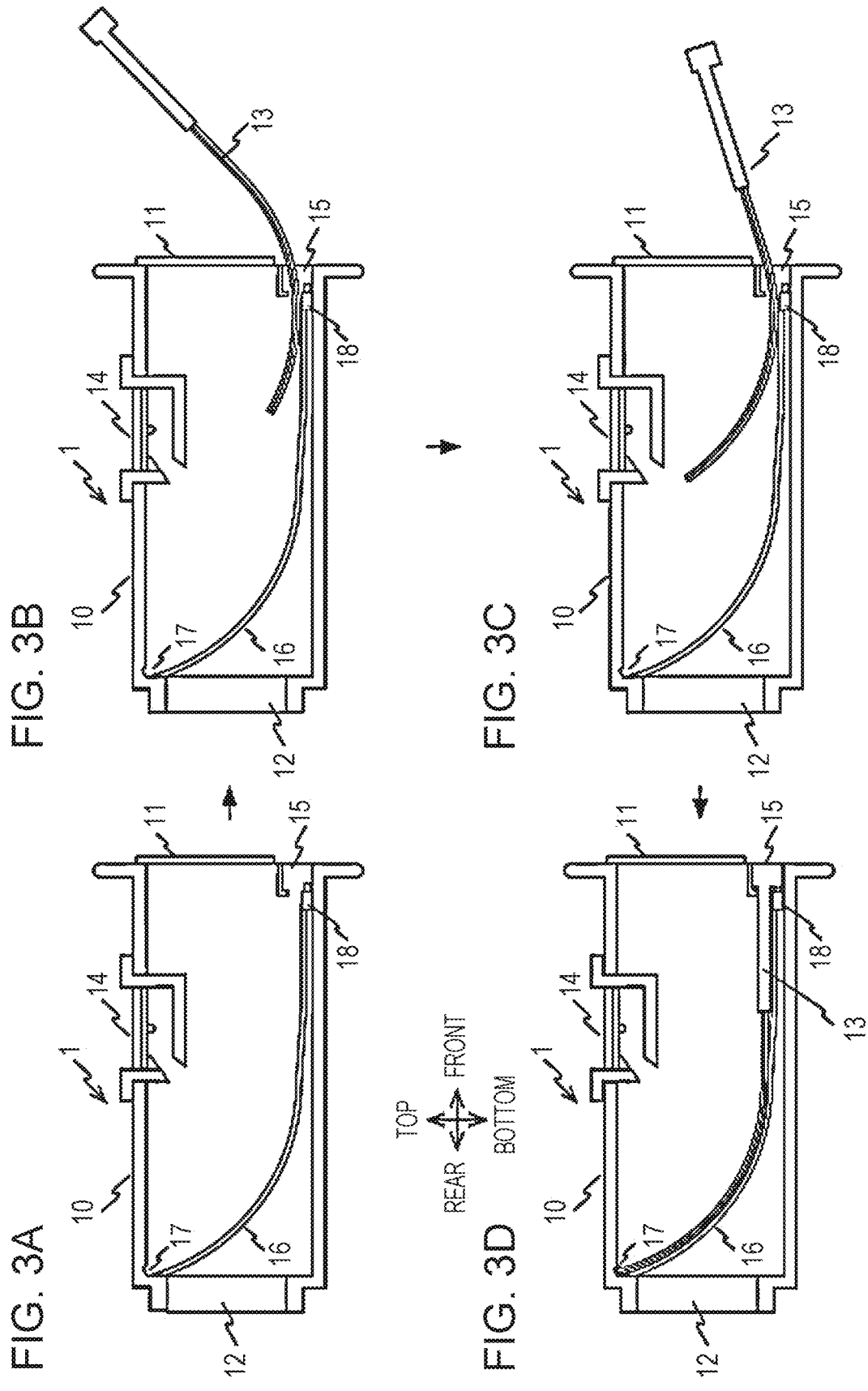
FIGS. 3A to 3D are diagrams illustrating a process of mounting the filter module according to the embodiment of the present disclosure.

FIG. 3A is a sectional view of the air-outlet unit 1, without the filter module 13, taken along line IIIA-IIIA of FIG. 1A2.

As illustrated in FIG. 3A, an opening 15 for introducing the filter module 13 into the hollow space of the main body 10 is formed in a lower portion of the front surface of the main body 10. The left and right inner walls of the hollow space of the main body 10 may have guides 16 that are formed in such a manner as to slightly project in a transverse direction toward the hollow space. The guides 16 may guide left and right side portions of the filter module 13, which is inserted through the opening 15, to predetermined positions and support the left and right side portions at the predetermined positions. An upper inner wall of the hollow space of the main body 10 has a groove 17 in which a front end portion of the filter module 13 is fitted when the filter module 13 is located at a predetermined position. In addition, a latch 18, such as a magnetic push latch, may be disposed at a position slightly behind the opening 15, and the filter module 13 that is located at the predetermined position in the hollow space of the main body 10 may be fixed in place at the predetermined position by the latch 18.

In such a configuration, when the filter module 13 is mounted for the first time, or when the filter module 13 is replaced, installation of the filter module 13 into the air-outlet unit 1 is performed in the following manner.

As illustrated in FIG. 3B, the front end portion of the filter module 13 is inserted into the opening 15, which is formed in the lower portion of the front surface of the main body 10, and the filter module 13 is inserted into the hollow space of the main body 10 while being rotated, as illustrated in FIG. 3B and FIG. 3C. When the filter module 13 enters and reaches the predetermined position illustrated in FIG. 3D, the front end portion of the filter module 13 is fitted into the groove 17, and the front thick portion of the filter module 13 is locked by the latch 18. Note that, in the case of using a magnetic push latch as the latch 18, a magnet or a ferromagnetic material is provided at the rear end of the front thick portion of the filter module 13.

When the latch 18 is locked, the filter module 13 is fixed in place at the predetermined position illustrated in FIG. 3D by the actions of the guides 16, the groove 17, and the latch 18.

Here, the predetermined position of the filter module 13, which is illustrated in FIG. 3D, is a position at which the filter module 13 is curved upward in a direction from its front end toward its rear end, so as to extend from the side on which a lower inner wall of the hollow space of the main body 10 is present, to a position near the upper inner wall of the hollow space of the main body 10, so that the hollow space of the main body 10 is roughly divided by the photocatalytic filter 132 into a space behind the photocatalytic filter 132, and a space in front of the photocatalytic filter 132. Thus, most of the air that flows into the main body 10 through the inflow port 12 of the main body 10 and passes through the fins 11, so as to be sent to the front side of the main body 10, passes through the photocatalytic filter 132.

When, for example, the filter module 13 is replaced, the filter module 13 can be removed from the air-outlet unit 1 through a process that is the reverse of the process of installing of the filter module 13. Note that, in the case of using a push latch, such as a magnetic push latch, as the latch 18, the filter module 13 is released from being restrained by the latch 18 by pushing the filter module 13 slightly backward.

As described above, according to the present embodiment, since the filter module 13 has a vertically curved shape, when viewed in the transverse direction, replacement of the filter module 13 can be performed by only inserting and extracting the filter module 13 into and from the main body 10 from the front surface side, and the maintainability of the filter module 13 is improved.

The light-source substrate 14 that is disposed on the upper portion of the main body 10 includes a light emitting diode (LED) array and a light-emission control device that controls light emission of the LED array.

Figures 4A, 4B:
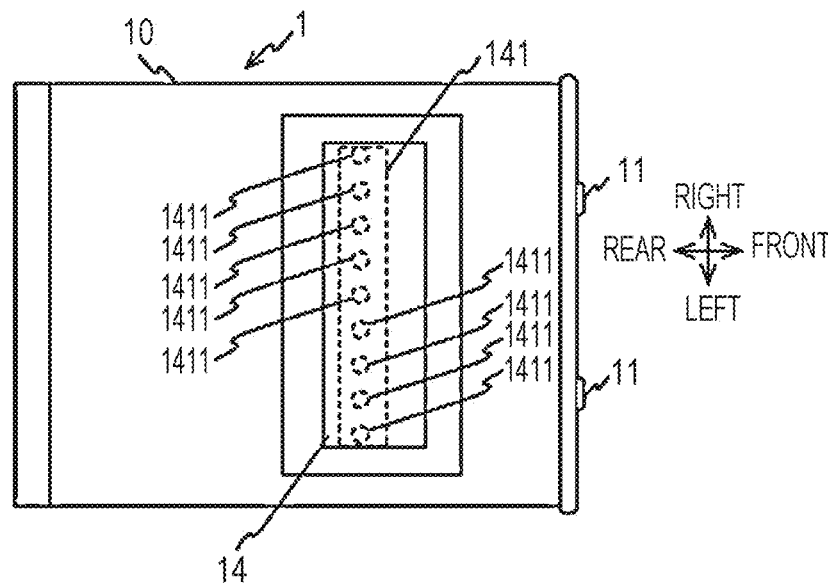
FIGS. 4A and 4B are diagrams illustrating the relationship between an LED array and a photocatalytic filter according to the embodiment of the present disclosure.

As illustrated in FIG. 4A, which is a sectional view of the air-outlet unit 1 taken along line IVA-IVA of FIG. 1A2, an LED array 141 is disposed on a lower surface of the light-source substrate 14 and radiates light onto the photocatalytic filter 132 in the hollow space of the main body 10, so as to activate the photocatalytic filter 132.

As illustrated in FIG. 4B, the LED array 141 includes a plurality of LEDs 1411 that are arranged in the transverse direction. Some of the LEDs 1411 emit white light, while the remaining LEDs 1411 emit blue light having a wavelength of around 460 nm.

The upper inner wall in the hollow space of the main body 10 is provided with a narrowing member 19 that limits an irradiation range of the LED array 141.

Here, the narrowing member 19 is disposed so as to limit the irradiation range of the LED array 141 in the following manner.

On the assumption that the top, bottom, front, and rear sides are defined as illustrated in FIG. 5A1 and FIG. 5A2, light that is incident on a position P on a curved surface illustrated in FIG. 5A1 and FIG. 5A2, the position P being located on a concave side of the curved surface, from a forward direction with respect to a direction VP from the position P toward the center of curvature CP of the curved surface, that is, a direction VP normal to the curved surface on the concave side at the position P, always reflects backward.

Note that the same applies to the case of a flat surface, and light that is incident on a position P on a flat surface illustrated in FIG. 5B1 and FIG. 5B2 from a forward direction with respect to a direction VP normal to the flat surface at the position P, always reflects backward. Accordingly, the narrowing member 19 is disposed to limit the irradiation range of the LED array 141 in such a manner that, in a region of the photocatalytic filter 132 of the filter module 13 at the predetermined position, the region being irradiated with the light emitted from the LED array 141, the light emitted from the LED array 141 is incident on each position only from a forward direction with respect to a direction from the position toward the center of curvature CP of the photocatalytic filter 132 at the position.

For example, when the photocatalytic filter 132 has a constant curvature, as illustrated in FIG. 5C, the narrowing member 19 is disposed to limit the irradiation range of the LED array 141 in such a manner that the light emitted from the LED array 141 is incident on each position in the region only from a forward direction with respect to the direction toward the center of curvature CP of the photocatalytic filter 132.

With this configuration, the possibility of a primary reflected-light component, that is the light emitted from the LED array 141 and reflected by the photocatalytic filter 132 passing through the fins 11 and transmitting to an area ahead of the air-outlet unit 1, can be reduced. Here, the intensity of the primary reflected-light component obtained by the photocatalytic filter 132 is relatively high, and thus, the safety of the air-outlet unit 1 is maintained by suppressing the transmission of the primary reflected-light component to the area ahead of the air-outlet unit 1.

Note that, for example, when the photocatalytic filter 132 is vertically disposed as illustrated in FIG. 5D, it is difficult to prevent the primary reflected-light component obtained by the photocatalytic filter 132 from passing through the fins 11 and transmitting to an area ahead of the air-outlet unit 1, while allowing most of the air to flow through the region of the photocatalytic filter 132 that is irradiated with the light emitted from the LED array 141.

Figure 6A:
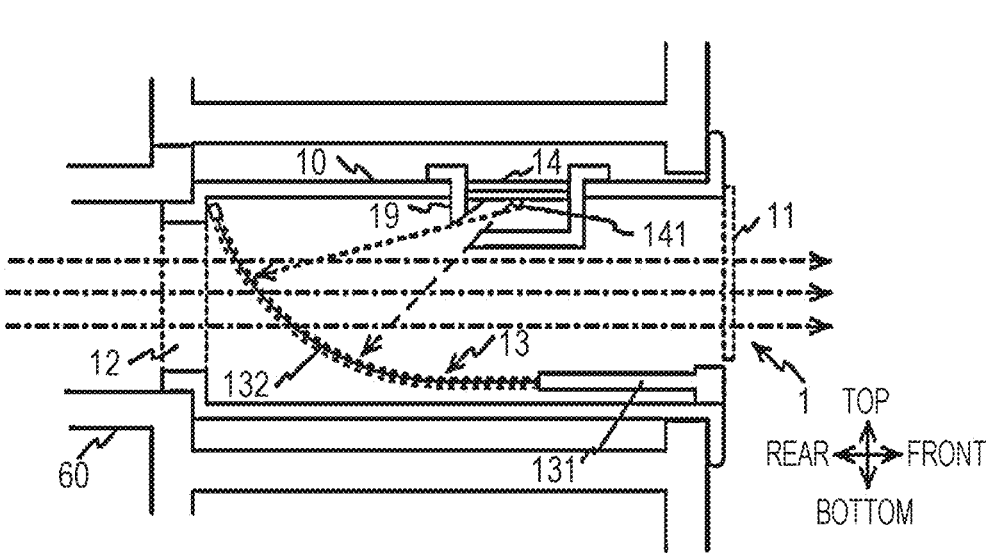
FIGS. 6A and 6B are diagrams illustrating the air-outlet unit according to the embodiment of the present disclosure attached to an air duct of an automobile.
Figure 6B:
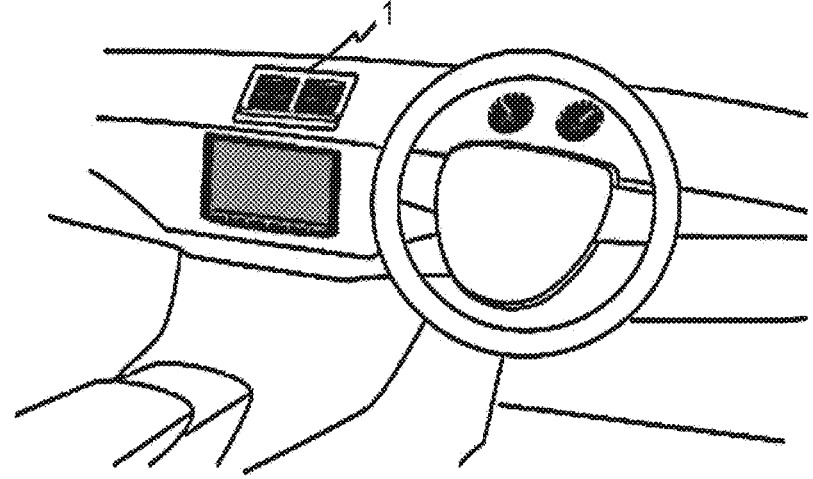

The air-outlet unit 1, which has been described above, is coupled to the air duct 60 of the air conditioner of the automobile, as illustrated in FIG. 6A, and forms the air outlet of the air conditioner of the automobile, as illustrated in FIG. 6B.

As illustrated in FIG. 6A, the air that is sent to the air-outlet unit 1 from the air duct 60 of the air conditioner of the automobile passes through the photocatalytic filter 132 and is supplied to the interior of the automobile by passing through the fins 11. The photocatalytic filter 132 is activated by the light emitted from the LED array 141, and the air that is supplied to the interior of the automobile from the air duct 60 is cleaned when it passes through the photocatalytic filter 132.

The light-emission control device that is included in the light-source substrate 14 will now be described.

Figure 7:
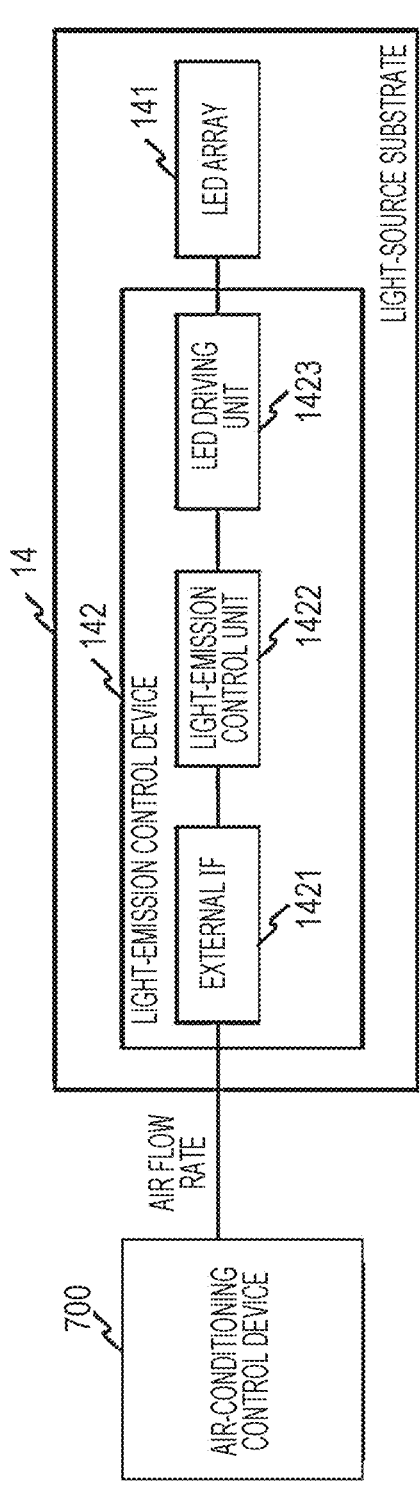
FIG. 7 is a block diagram illustrating the configuration of a light-emission control device according to the embodiment of the present disclosure.

FIG. 7 illustrates the configuration of a light-emission control device 142.

As illustrated in FIG. 7, the light-emission control device 142 includes an external interface 1421, a light-emission control unit 1422, and an LED driving unit 1423. In some implementations, any one or more of the functional blocks 142, 1422, and/or 1423 described above can be implemented, in whole or in part, by any of hardware, a digital signal processor (DSP), and/or software. For example, in a case where a functional block is configured by software, each such functional block may include, for example, a CPU, a RAM, and a ROM of a computer, whether dedicated or shared, and is achieved by operation of a program stored in a recording medium, such as a RAM, a ROM, a hard disk, or a semiconductor memory.

The external interface 1421 is connected to an air-conditioning control device 700 that controls the air conditioner of the automobile and obtains the most recent airflow rate of the air conditioner from the air-conditioning control device 700. Like the light-emission control device, the air-conditioning control device 700 may be implemented, in whole or in part, by any of hardware, a digital signal processor (DSP), and/or software. For example, in a case where configured by software, the control device 700 may comprise, for example, a CPU, a RAM, and a ROM of a computer, whether dedicated or shared, and is achieved by operation of a program stored in a recording medium, such as a RAM, a ROM, a hard disk, or a semiconductor memory.

The light-emission control unit 1422 outputs a pulse width modulation (PWM) signal that controls the amount of light of the LED array 141 to the LED driving unit 1423 in accordance with the airflow rate obtained by the external interface 1421.

The LED driving unit 1423 drives the LED array 141 in accordance with a PWM signal so as to cause the LED array 141 to emit light.

Here, the light-emission control unit 1422 performs control according to the airflow rate, which is obtained by the external interface 1421, in the following manner.

Figure 8A:
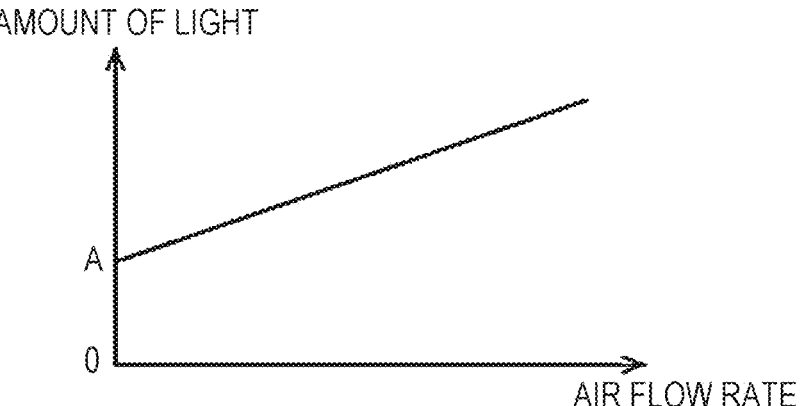
FIGS. 8A and 8B are graphs illustrating the way in which light-emission control according to the embodiment of the present disclosure is performed.

The light-emission control unit 1422 controls the amount of light, which is emitted from the LED array 141, by using a PWM signal in such a manner that the amount of light from the LED array 141 increases as the airflow rate of the air conditioner increases, as illustrated in FIG. 8A.

Figure 8B:
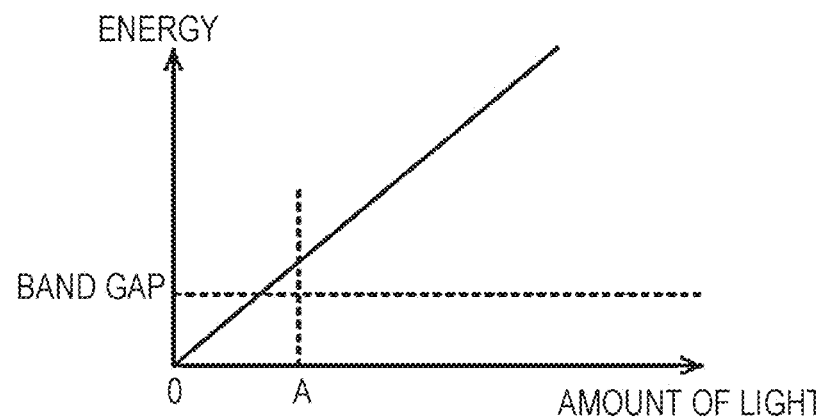

As illustrated in FIG. 8B, when the amount of light the LED array 141 increases and the amount of light that is radiated onto the photocatalytic filter 132 increases, energy greater than the bandgap of a photocatalyst increases, and the photocatalytic filter 132 is further activated, so that the air cleaning performance increases.

Thus, as mentioned above, the amount of light that is emitted from the LED array 141 increases as the airflow rate of the air conditioner increases, so that, in the case where a sufficient air cleaning effect is obtained with a low airflow rate and a relatively low air cleaning performance, energy saving of the LED array 141 and extension of the service life of the LED array 141 can be achieved by reducing the amount of light from the LED array 141. In the case where the airflow rate is high and where a relatively high air cleaning performance is necessary in order to obtain a sufficient air cleaning effect, the sufficient air cleaning effect can be ensured by increasing the amount of light the LED array 141.

Therefore, according to the present embodiment, energy saving of the LED array 141 and extension of the service life of the LED array 141 can be achieved, while a favorable air cleaning effect is obtained regardless of the airflow rate.

As described above, in order to ensure safety, the air-outlet unit 1 of the present embodiment reduces the possibility of the primary reflected-light component, which is the light emitted from the LED array 141 and reflected by the photocatalytic filter 132 and which has a relatively high intensity, from transmitting to an area ahead of the air-outlet unit 1.

Figure 9:
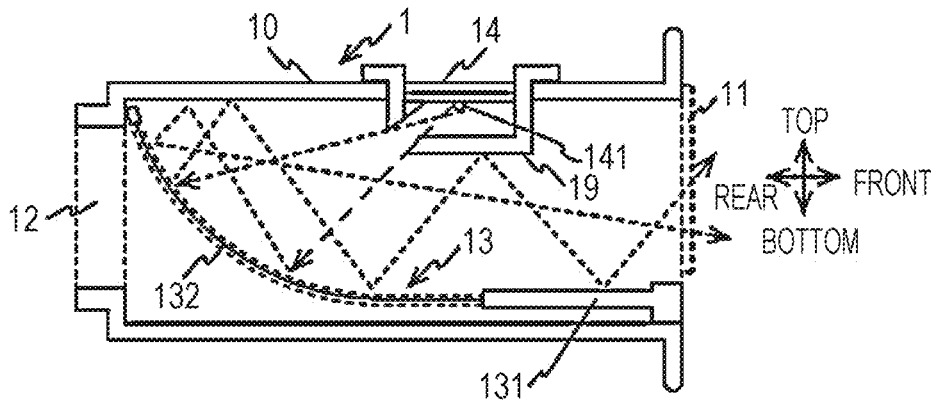
FIG. 9 is a diagram illustrating secondary and subsequent reflected light components according to the embodiment of the present disclosure.

On the other hand, as illustrated in FIG. 9, the air-outlet unit 1 of the present embodiment is configured such that portions of secondary and subsequent reflected light components each having a relatively low intensity, such as a secondary reflected-light component that is the reflected light of the primary reflected-light component, and a tertiary reflected-light component that is the reflected light of the secondary reflected-light component, pass through the fins 11 and transmit to an area ahead of the air-outlet unit 1.

Here, since the LED array 141 emits white light and blue light, the light of the LED array 141 is visible and is perceived by a user as blue light.

Thus, a user can directly perceive an air cleaning operation by the light that transmits to the area ahead of the air-outlet unit 1.

In addition, as the air cleaning that is performed becomes stronger, the intensity of the light that transmits to the area ahead of the air-outlet unit 1 is increased by the above-mentioned control of the amount of light from the LED array 141, and thus, the user can also directly and dynamically perceive the degree of the air cleaning by the intensity of this light.

Therefore, without adding any special device to the air-outlet unit 1, the user can directly perceive the air-cleaning operation of the air-cleaning device.

In general, blue evokes a color emotion that enhances concentration, and a color emotion that leads to calmness or quietness, and thus, the blue light that transmits forward from the air-outlet unit 1 can provide a favorable decorative effect and improve the psychological stability of a user.

The embodiment of the present disclosure has been described above.

Figure 10A:
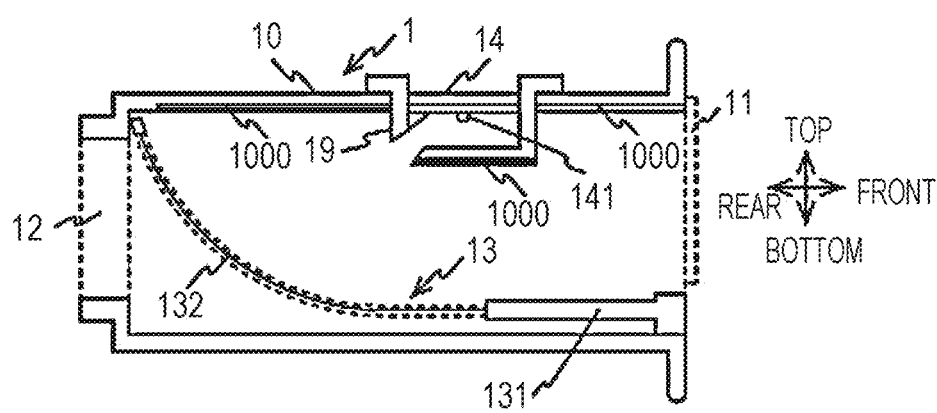
FIGS. 10A and 10B are diagrams illustrating another configuration example of the air-outlet unit according to the embodiment of the present disclosure.

As illustrated in FIG. 10A, in the air-outlet unit 1 of the above-described embodiment, an optical member 1000 such as a reflecting plate or a scattering plate that increases the secondary and subsequent reflected light components that transmit to the area ahead of the air-outlet unit 1 may be disposed in the hollow space.

Figure 10B:
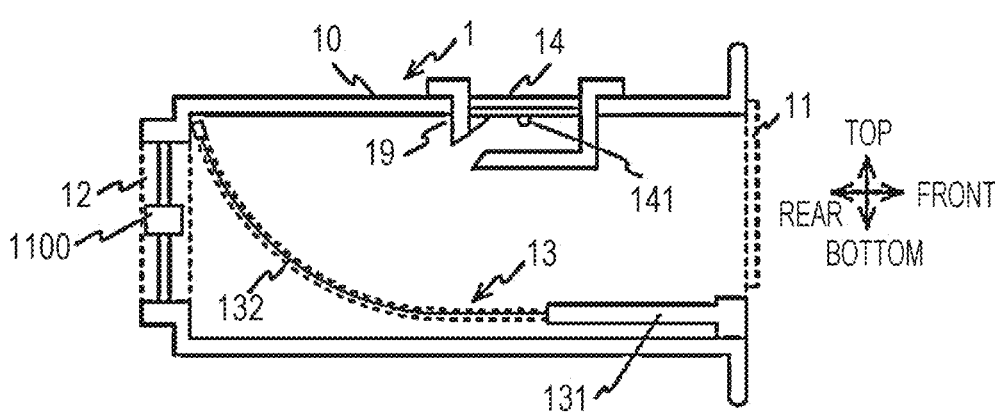

In addition, in the above-described embodiment, although the light-emission control unit 1422 controls the amount of light from the LED array 141 in accordance with the airflow rate received from the air-conditioning control device 700, an airflow rate sensor 1100 that detects the flow rate of the air blown by the air conditioner may be included in the air-outlet unit 1, as illustrated in FIG. 10B, and the light-emission control unit 1422 may control the amount of light from the LED array 141 in accordance with the airflow rate detected by the airflow rate sensor 1100 in such a manner that the amount of light increases as the airflow rate increases.

In some embodiment, the structure of the air-outlet unit 1 may be turned upside down. In other words, the opening 15 of the main body 10 into which the filter module 13 is inserted may be formed at a position above the fins 11, and the filter module 13 may have a shape that is curved downward toward the rear side.

In addition, in some embodiments, a structure that is obtained by turning upside down and switching the left and right sides of the above-described structure, excluding the arrangement of the fins 11 of the air-outlet unit 1, may be employed. In other words, the opening 15 into which the filter module 13 is inserted may be formed at a position on the left-hand side of the fins 11, and the filter module 13 may have a shape that is curved rightward toward the rear side. Alternatively, the opening 15 into which the filter module 13 is inserted may be formed at a position on the right-hand side of the fins 11, and the filter module 13 may have a shape that is curved leftward toward the rear side.

The above-described configuration of the air-outlet unit 1 is not limited to being applied to the air-outlet unit 1 that forms an air outlet of an air conditioner of an automobile, and can instead be applied as a configuration of an air outlet of an arbitrary air cleaning device. In addition, the above-described configuration of the air-outlet unit 1 for controlling the amount of light in accordance with an airflow rate can be applied to an arbitrary air cleaning device that uses a photocatalyst.

Although there has been illustrated and described what is at present contemplated to be preferred embodiments of the present disclosure, it will be understood by those skilled in the art that various changes and modifications may be made, and equivalents may be substituted for elements thereof without departing from the true scope of the disclosure. In addition, many modifications may be made to adapt a particular situation to the teachings of the disclosure without departing from the central scope thereof. Therefore, it is intended that this disclosure not be limited to the particular embodiments disclosed, but that the disclosure will include all embodiments falling within the scope of the appended claims.

What is claimed is:

1. An air cleaning device having an air supply port through which air is blown from an inner space to outside of the air cleaning device, the air cleaning device comprising:

a light emitting diode (LED) that emits light to the inner space;

a photocatalytic filter that is disposed in the inner space and that cleans air blown by the air cleaning device by being activated by light emitted from the LED;

an airflow rate sensor that detects a flow rate of the air blown by the air cleaning device;

a light-amount control unit that controls an amount of light that is emitted from the LED, wherein the light-amount control unit controls the amount of light that is emitted from the LED in such a manner that the amount of light increases as the airflow rate detected by the airflow rate sensor increases; and, a fin assembly positioned at the air supply port and a narrowing member disposed between the LED and the photocatalytic filter, the narrowing member defining an irradiation aperture oriented so that (i) light emitted by the LED is directly incident on the photocatalytic filter and does not directly transmit to the air supply port, (ii) light primarily reflected by the photocatalytic filter does not directly transmit through the air supply port, and (iii) at least a portion of secondary and subsequent reflected light components are permitted to transmit through the fin assembly to outside of the air cleaning device.

2. The air cleaning device according to claim 1, wherein the LED emits visible light.

3. The air cleaning device according to claim 1, further comprising an optical member disposed within the inner space configured to increase secondary and subsequent reflected light components that transmit through the fin assembly to outside of the air cleaning device.

4. The air cleaning device according to claim 3, wherein the LED emits visible blue light.

5. The air cleaning device according to claim 1, wherein the air cleaning device forms an air outlet of an air conditioner of an automobile.

* * * * *